(12) United States Patent
Medoff

(10) Patent No.: US 11,529,174 B2
(45) Date of Patent: Dec. 20, 2022

(54) METHOD FOR CHANGING A CONFIGURATION OF A BONE

(71) Applicant: TriMed, Incorporated, Santa Clarita, CA (US)

(72) Inventor: Robert Medoff, Kailua, HI (US)

(73) Assignee: TriMed, Incorporated, Santa Clarita, CA (US)

( * ) Notice: Subject to any disclaimer, the term of this patent is extended or adjusted under 35 U.S.C. 154(b) by 572 days.

(21) Appl. No.: 16/460,626

(22) Filed: Jul. 2, 2019

(65) Prior Publication Data

US 2020/0008846 A1    Jan. 9, 2020

Related U.S. Application Data

(60) Provisional application No. 62/693,516, filed on Jul. 3, 2018.

(51) Int. Cl.
*A61B 17/80* (2006.01)
*A61B 17/68* (2006.01)
*A61B 17/56* (2006.01)

(52) U.S. Cl.
CPC .... *A61B 17/8019* (2013.01); *A61B 2017/564* (2013.01); *A61B 2017/681* (2013.01)

(58) Field of Classification Search
CPC .............. A61B 17/151; A61B 17/8019; A61B 2017/564; A61B 2017/681
See application file for complete search history.

(56) References Cited

U.S. PATENT DOCUMENTS

| | | |
|---|---|---|
| 3,244,170 A | 4/1966 | McElvenny |
| 3,386,437 A | 6/1968 | Treace |
| 3,400,711 A | 9/1968 | Hux et al. |
| 3,604,414 A | 9/1971 | Borges et al. |
| 6,007,535 A | 12/1999 | Rayhack et al. |
| 8,579,898 B2 * | 11/2013 | Prandi ................ A61B 17/8061 606/280 |

(Continued)

FOREIGN PATENT DOCUMENTS

| | | |
|---|---|---|
| CN | 105 640 627 A | 6/2016 |
| CN | 108078618 A | 5/2018 |

(Continued)

OTHER PUBLICATIONS

International Preliminary Report on Patentability and Written Opinion of the ISA, dated Jan. 5, 2021 in International Application No. PCT/US2019/040347.

(Continued)

*Primary Examiner* — Anu Ramana
(74) *Attorney, Agent, or Firm* — Wood, Phillips, Katz, Clark & Mortimer

(57) ABSTRACT

A method and apparatus for changing a configuration of a bone. The method includes the steps of: fixing a first part of a bone plate to the bone at a first location; securing a guide assembly in an operative position in relationship to the bone; engaging a bone part moving assembly with the bone at a second bone location spaced from the first bone location; cutting the bone to define first and second bone sections and so that the bone part moving assembly engages the second bone section and the first bone location is on the first bone section; relatively repositioning the first and second bone sections into a desired relationship and thereby causing a part of the bone part moving assembly to move guidingly, together with the second bone section, in a controlled path; and fixing the first and second bone sections in the desired relationship. The first and second bone sections can be controllably relatively moved lengthwise of the bone plate without requiring guided movement of any component that extends through the bone plate and into the bone.

21 Claims, 10 Drawing Sheets

(56) References Cited

U.S. PATENT DOCUMENTS

| | | | | |
|---|---|---|---|---|
| 8,652,142 | B2* | 2/2014 | Geissler | A61B 17/15 606/87 |
| 8,915,924 | B2* | 12/2014 | Appenzeller | A61B 90/39 606/96 |
| 9,351,742 | B2* | 5/2016 | Appenzeller | A61B 17/1728 |
| 9,452,004 | B2* | 9/2016 | Larche | A61B 17/8019 |
| 9,808,297 | B2* | 11/2017 | Bernstein | A61B 17/1728 |
| 2007/0276383 | A1 | 11/2007 | Rayhack | |
| 2009/0131987 | A1 | 5/2009 | Matityahu | |
| 2011/0238068 | A1 | 9/2011 | Bernsteiner | |

FOREIGN PATENT DOCUMENTS

| | | |
|---|---|---|
| DE | 10 2011 106172 A1 | 1/2013 |
| WO | 2015/138542 A2 | 9/2015 |

OTHER PUBLICATIONS

Office Action dated Nov. 25, 2021 in Chinese Patent Application No. 2019800571598.
Office Action dated Sep. 10, 2021 in Australian Patent Application No. 2019299440.
"Surgical Technique—Step By Step, Ulna Shortening System 2.5, APTUS® Wrist", WRIST-10010001_V6, Jun. 2017, Medartis AG, Switzerland.
International Search Report and Written Opinion, dated Sep. 20, 2019 in International Patent Application No. PCT/US19/40347.
Supplementary European Search Report, dated Mar. 11, 2022 in European Patent Application No. EP 19 83 1539.

* cited by examiner

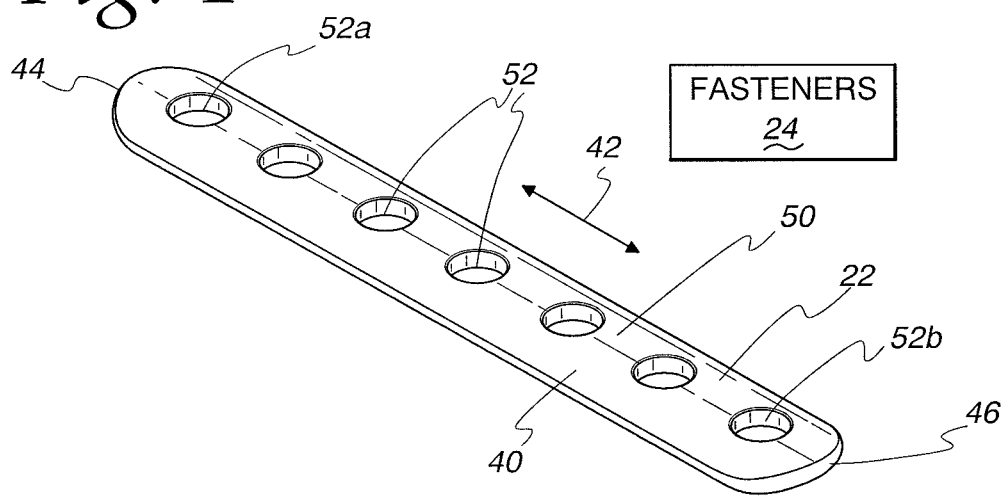
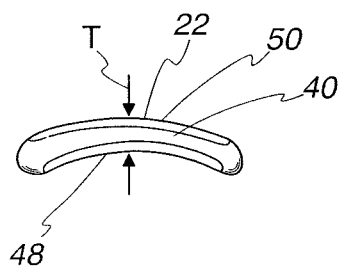
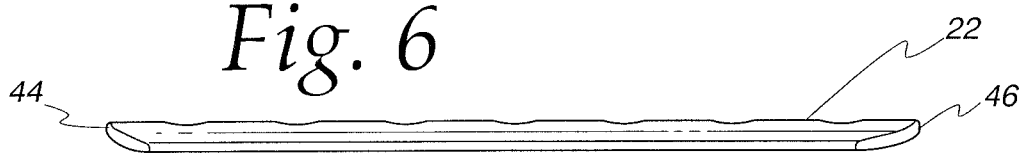
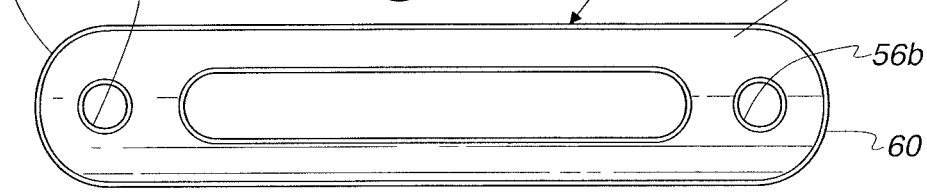

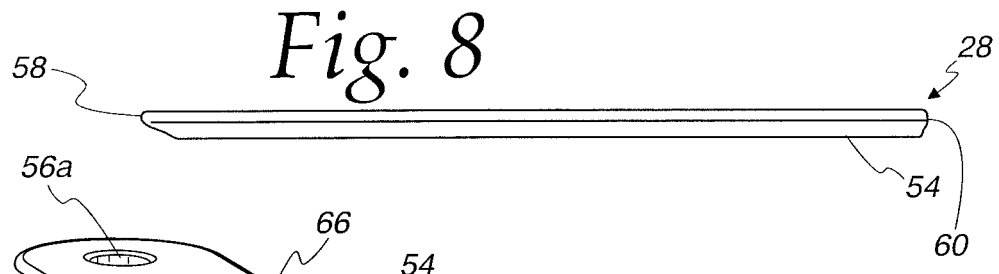
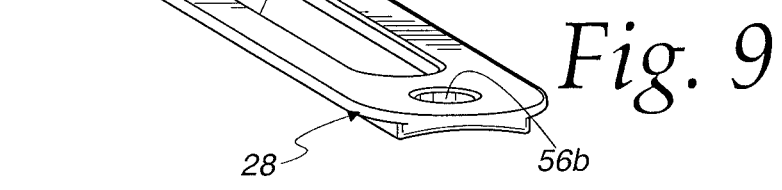
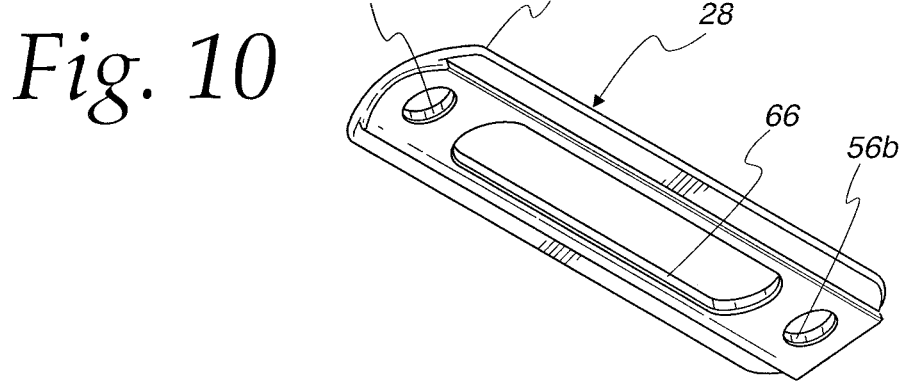
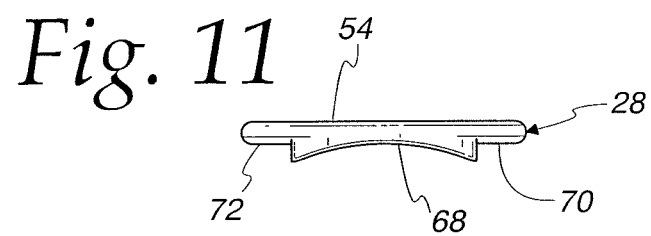
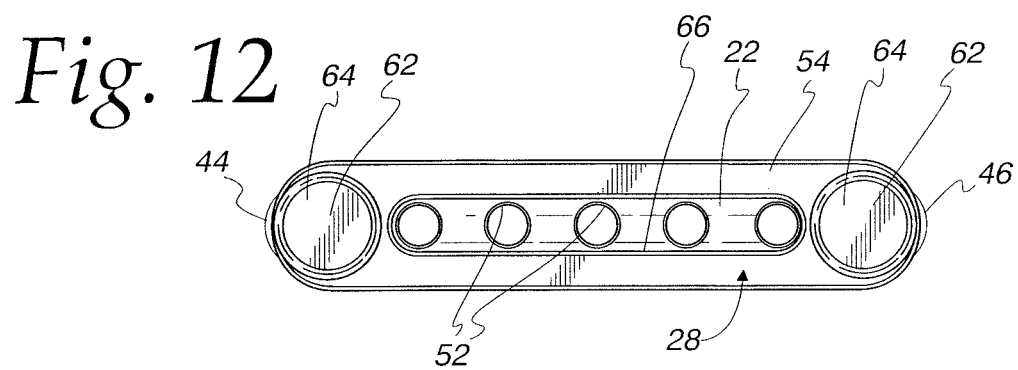

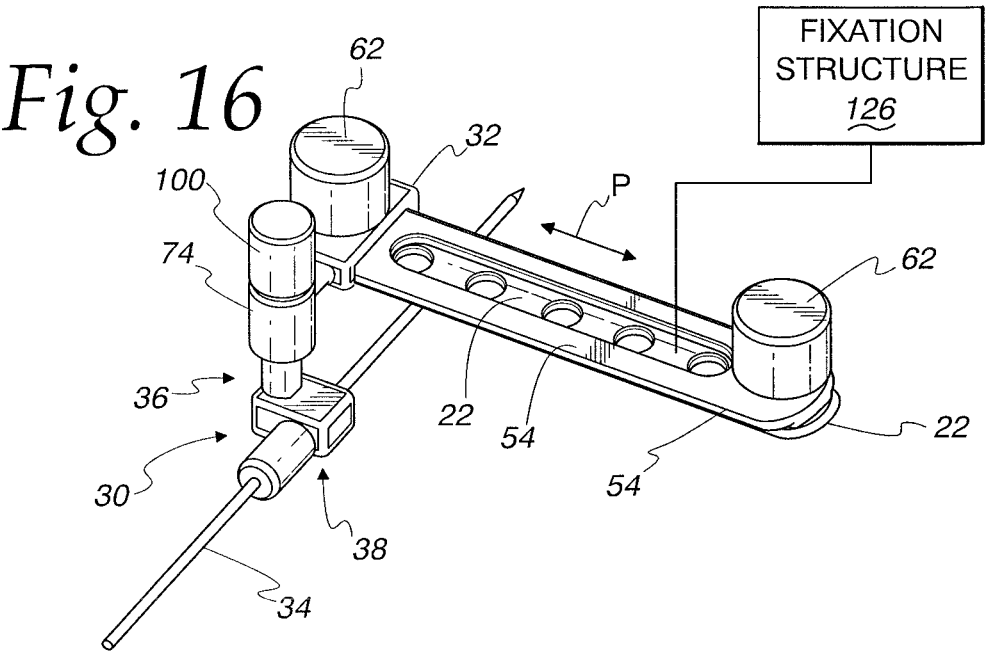
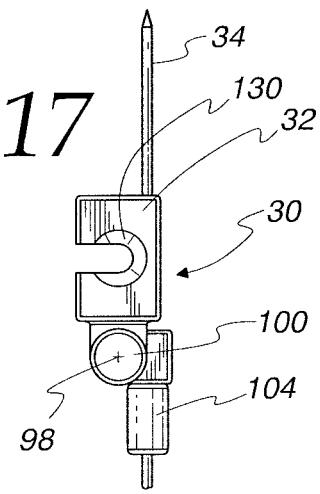
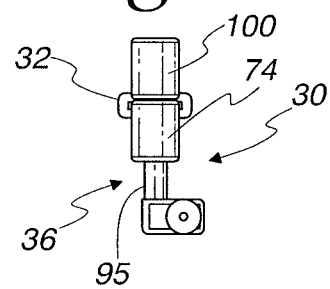
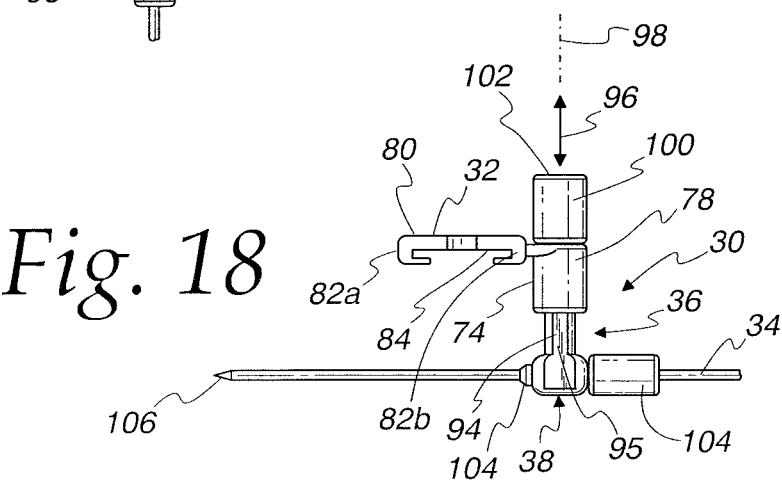

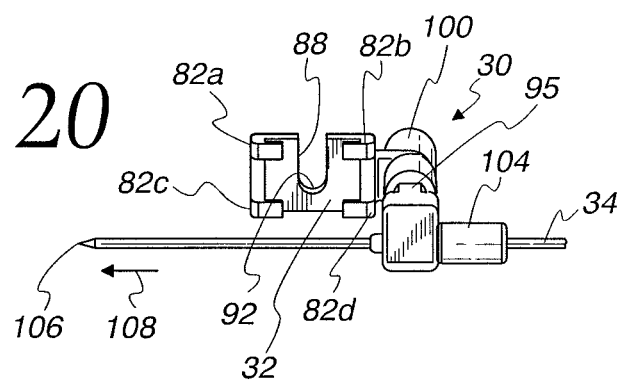
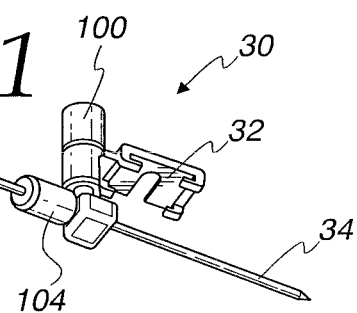
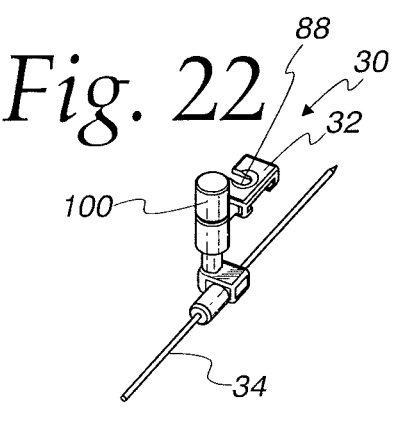
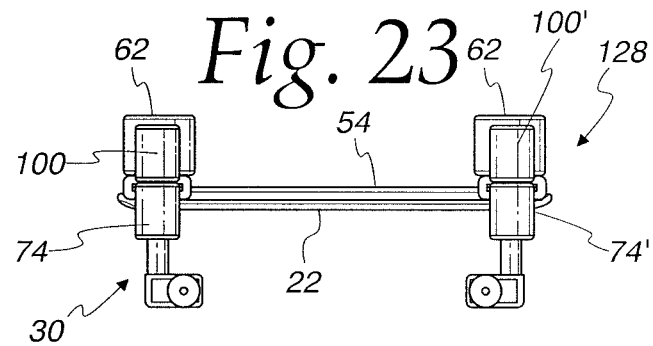
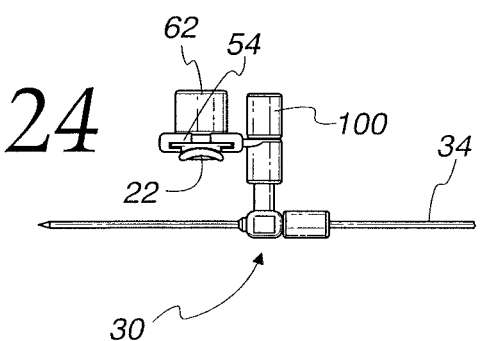

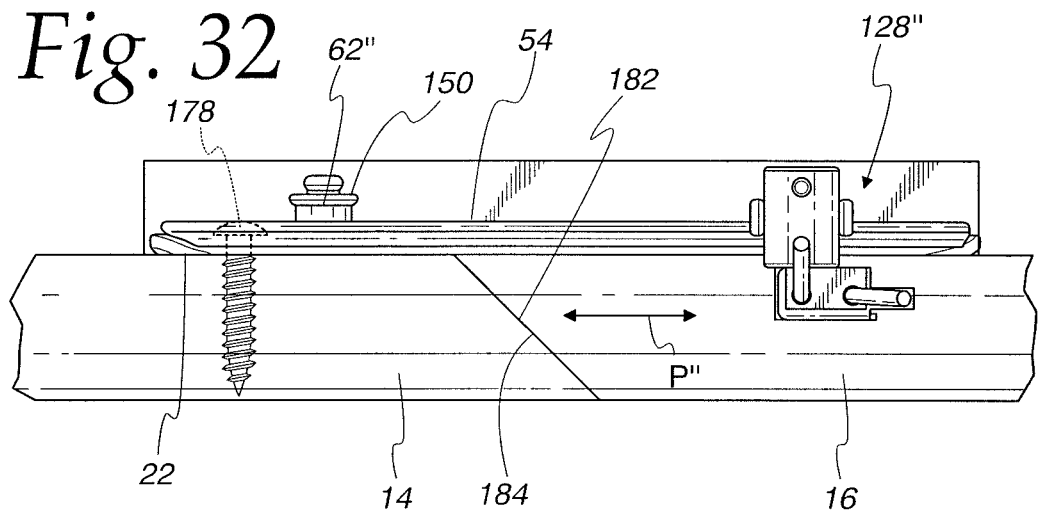
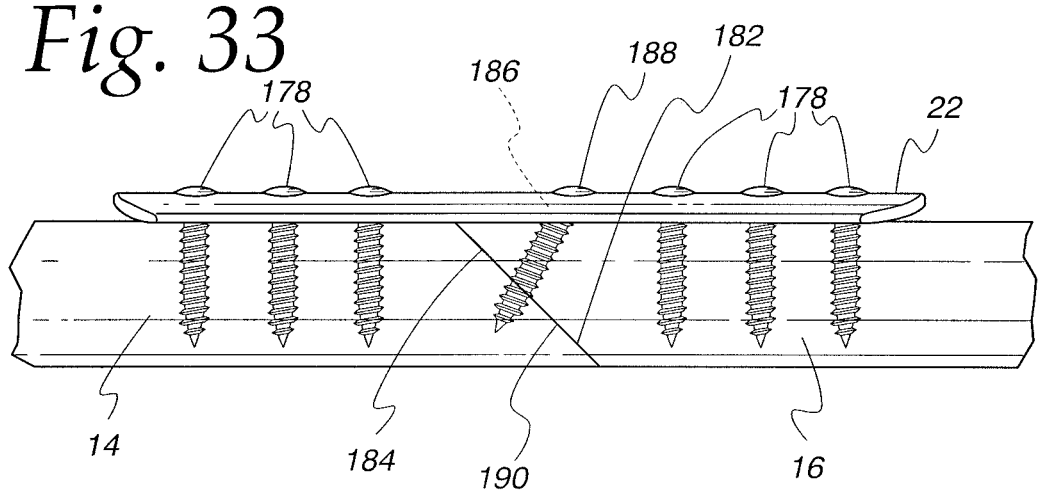
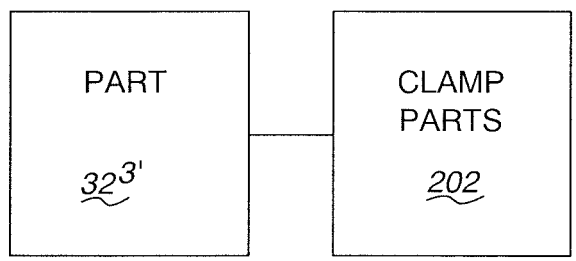

METHOD FOR CHANGING A CONFIGURATION OF A BONE

BACKGROUND OF THE INVENTION

Field of the Invention

This invention relates to surgical instrumentation and procedures and, more particularly, to a method and system for changing the configuration of a bone.

Background Art

Bone osteotomies (i.e., procedures involving cutting bone) are used to correct malalignment of osseous structures in the human skeleton. This procedure is commonly used to correct malalignment of rotation, translation, or excessive/inadequate length of the bone involved. When used to correct excessive or inadequate axial length of the bone, the procedure is categorized as a lengthening or shortening osteotomy. Osteotomies to gain or reduce length may be done in any bone; a common example in the upper extremity is called an ulnar shortening procedure. This procedure is done to correct excessive ulnar length causing the distal end of the bone to abut against the bones of the wrist. The prior art will be described hereinbelow with respect to an ulnar shortening procedure. The ulna is just representative of many different bones that have been similarly treated. Further, bone shortening, as described below, is likewise but a representative procedure that involves bone cutting.

The first description of ulnar shortening used a free hand technique where a segment of bone was simply cut transversely without a guide and the bones brought manually together and fixed. This required free hand precision to ensure that the cuts were exactly parallel, and created challenges in accurately aligning and fixing two highly unstable segments of bone by hand. Later modifications in the technique included making an oblique or step cut to provide at least some control of the unstable end and aid in precise alignment (particularly rotation) between the bone segments as they were apposed. However, these methods still require the surgeon to have a high level of skill and ability to create precisely cut surfaces that match perfectly, as well as ensure that bone ends are placed in accurate apposition and alignment. Uneven cuts or misjudging the size of the resected segment can be common, and result in non-unions, malunions, and/or inadequate or excessive correction of the deformity.

The Rayhack system was the first significant instrumentation system that employed a sequence of guides to try to improve the precision of cuts and simplify alignment and fixation of the bone ends for ulnar shortening osteotomies. With this system, the surgeon first attaches a saw guide to the bone with screws; this guide is then used to create precise, accurate oblique cuts to remove a predetermined length of bone and create parallel bone surfaces. The guide is then removed and a bone plate applied across the unstable segments. A compression block is then fixed with an extra long screw on one side. A screw is placed into a slotted hole through the bone plate at the other end of the plate and compression clamp thumbscrews tightened to bring the two sides of the compression block together, shortening the bone by the sliding action of the screw in the sliding hole of the plate. Additional screws are placed into the plate and the first screws removed to remove the block and replaced with appropriate length screws.

Although this system was a significant advance in the technique of ulnar shortening and removed much of the imprecision and guesswork of freehand cuts and guiding the bone resection, it is cumbersome and complicated. For example, the technique brochure for this technique lists a total of fifteen separate steps in order to complete the procedure. Second, it requires that the guide is physically screwed into the bone, adding time to the procedure, and requires screws to be placed and removed multiple times into a single hole, which can compromise thread purchase. Yet another issue is the need for removal of the guide and then application of the plate, which requires the surgeon to deal with aligning two grossly unstable bone and freely moveable bone segments during the procedure. He/she still needs to provisionally hold the plate on these unstable pieces as fixation screws are placed. The plate requires a bone screw through a slotted hole; this bone screw is loosened and the shortening done by allowing the screw (which is attached to the bone) to slide within the slotted hole. The screw is then tightened—these steps of inserting, then loosening, then compressing through this loose screw, then re-tightening can adversely distort the threaded bone hole and compromise fixation by the screw.

TriMed, Inc., the assignee herein, developed another ulnar shortening system that improved on the Rayhack system to overcome some of the above issues. In this system, a plate is first secured on one side of the anticipated cut with three bone screws (the fixed segment), and a single screw at the end of a slotted hole is placed on the opposite side (what will become the sliding segment). The plate has two additional pin slots through which pins are placed to prevent angular movement of the sliding segment after a cut is made.

A saw guide is attached using two holes along the side of the plate and used to make the bone cuts (one at a time). At the center of the plate, the undersurface is undercut to allow full oscillation of a saw blade to ensure that the cut is completely through the bone surface that sits under the plate. Compression is accomplished by using an instrument that attaches to one of the holes along the edge of the fixed side of the plate and the bone on the sliding side with a transverse pin. The bone screw in the sliding hole of the plate and vertical anti-rotation pins guide the movement of the sliding segment to shorten the bone and precisely appose the surfaces to allow the surgeon to complete fixation.

Although a significant improvement on the Rayhack system in terms of simplicity, precision and reproducibility over a wide variation of surgeon experience and ability, the TriMed system still has some features that could be improved. Since the plate is applied before the cut is made (as opposed to the Rayhack system), the plate has a cutout at the center of its undersurface to allow complete movement of the saw blade to fully divide the bone at the edge under the plate. This feature, along with the need for the pin holes along the edge of the plate to allow attachment of the guide and compression instrument during the procedure, requires that the plate have at least a certain thickness in order to accommodate these features. This may make the plate thicker than desirable for bone fixation and may result in increased soft tissue prominence which can require later removal as well as cause stress shielding of the bone under the plate (that can lead to later fracture). In addition, the need for a slotted bone screw hole and pin slots to allow the shortening add to the overall plate length and require a relatively long incision of corresponding length in order to apply the plate. Furthermore, the need for slotted holes for the screws and pins results in a significant separation between the final bone screw in the slotted hole and the osteotomy site, which is not optimal for fixation (biomechanically better to have fixation screws spread out in each bone segment, starting relatively close to the osteotomy site). Finally, guiding the bone shortening by movement of bone fixation elements through slotted holes in the plate limits the maximal length of shortening to the length of the slots. The system also places a lag screw across the oblique osteotomy cut, and the specific design of the plate requires the direction of the cut and direction of the lag screw to be placed in a single orientation. As some surgeons prefer the cut direction and lag screw in the opposite direction than provided, the system may not meet their needs. Because of the nature of the design which requires multiple screws on either side of the cut, the system is best suited to osteotomies in the center of a long bone, as opposed to osteotomies at the end of the bone where only a short segment on one side is available.

Variations in the basic TriMed-style plate have been made that include minor changes and improvements to the implant shortening system.

The challenge of allowing cutting fully through a bone without interference from the bone plate and/or any other component used to assist the performance of bone osteotomies persists to this day. As a result, surgeons have been required to use thicker bone plates, as described above, that may be configured to produce a gap region for a cutting component to enter, or to try and carefully maneuver a cutting component through a bone so that it does not impinge upon the bone plate or other structure used to assist the performance of an osteotomy. The former approach requires use of an undesirably thick bone plate whereas the latter requires highly skilled and careful maneuvering of a cutting instrument which may complicate and lengthen the performance period, for a particular procedure.

The industry continues to work on different systems and techniques that address one or more of the above areas.

SUMMARY OF THE INVENTION

In one form, the invention is directed to a method of changing a configuration of a bone having a length. The method includes the steps of: obtaining a bone plate having a length; fixing a first part of the bone plate to the bone at a first bone location; obtaining a guide assembly; securing the guide assembly in an operative position in relationship to the bone; obtaining a bone part moving assembly configured so that at least a part of the bone part moving assembly cooperates with the guide assembly to be guided in a controlled path by the guide assembly; engaging the bone part moving assembly with the bone at a second bone location spaced from the first bone location; cutting the bone to define first and second bone sections and so that the bone part moving assembly engages the second bone section and the first bone location is on the first bone section; relatively repositioning the first and second bone sections into a desired relationship and thereby causing the part of the bone part moving assembly to move, together with the second bone section, in the controlled path; and fixing the first and second bone sections in the desired relationship. The guide assembly and bone part moving assembly are configured so that with the guide assembly in the operative position and the bone part moving assembly engaged with the bone at the second location, relative movement of the first and second bone sections is guided in a direction lengthwise of the plate without requiring guiding by any component extended through the bone plate.

In one form, the guide assembly is integrally formed with the bone plate.

In one form, the guide assembly is separate from, and attached to, the bone plate.

In one form, the bone plate has at least one through opening to receive a fastener. The step of fixing the first and second bone sections in the desired relationship consists of obtaining at least one fastener and directing the at least one fastener into the at least one through opening in the bone plate and into the bone.

In one form, the method further includes the step of separating and removing at least part of the bone part moving assembly after fixing the first and second bone sections in the desired relationship.

In one form, the step of securing the guide assembly in an operative position involves securing the guide assembly to the bone plate.

In one form, there is an elongate rail on one of the guide assembly and the part of the bone part moving assembly and a cooperating slot on the other of the guide assembly and the part of the bone part moving assembly. The step of relatively positioning the first and second bone sections causes guided movement of the rail within the cooperating slot to thereby cause the part of the bone part moving assembly to be guided in the controlled path.

In one form, the part of the bone part moving assembly has a frame. The step of fixing the guide plate to the bone plate consists of directing a fastener through the guide plate and into the bone plate. The frame has an opening through which the fastener extends.

In one form, the bone part moving assembly has a fixation element support. The step of engaging the bone part moving assembly with the bone at the second location involves directing a fixation element, supported by the fixation element support, into the bone at the second location whereby the fixation element follows movement of the part of the bone part moving assembly in the controlled path.

In one form, the part of the bone part moving assembly is part of a frame. The fixation element support has a fixation element mount. The frame and fixation element support are configured so that the fixation element support is movable guidingly relative to the frame. The method further includes the step of moving the fixation element support relative to the frame so that the fixation element mount is at a desired location, within a range of potential locations after which the fixation element is directed into the bone.

In one form, the rail and cooperating slot are configured to produce a captive rail arrangement.

In one form, the method further includes the step of manipulating the bone part moving assembly to thereby effect relative repositioning of the first and second bone sections.

In one form, the method further includes the steps of obtaining a bone attachment assembly, engaging the bone attachment assembly with the guide assembly, and manipulating the bone part moving assembly and the bone attachment assembly to thereby effect relative repositioning of the first and second bone sections.

In one form, the bone attachment assembly has a frame. The guide assembly and frame are configured so that the frame is movable guidingly relative to the bone plate along the length of the bone plate.

In one form, the method further includes the step of fixing the frame to the bone at a location spaced from the second bone location before manipulating the bone part moving assembly and the bone attachment assembly to effect relative repositioning of the first and second bone sections.

In one form, the bone attachment assembly has a fixation element support. The method further includes the step of directing a fixation element, supported by the fixation element support, into the bone without passing through the bone plate.

In one form, the fixation element support has a fixation element mount. The frame and fixation element support are configured so that the fixation element support is movable guidingly relative to the frame. The method further includes the step of moving the fixation element support relative to the frame so that the fixation element mount is at a desired location within a range of potential locations after which the fixation element is directed into the bone.

In one form, the bone attachment assembly has a frame and a fixation element support with a fixation element mount. The frame and fixation element support are configured so that fixation element support is movable guidingly relative to the frame. The method further includes the step of moving the fixation element support relative to the frame so that the fixation element mount is at a desired location within a range of potential locations, after which the fixation element is directed into the bone.

In one form, the method further includes the step of obtaining a bone attachment assembly, engaging the bone attachment assembly with the guide assembly, and manipulating the bone part moving assembly and the bone attachment assembly to thereby effect repositioning of the first and second bone sections, wherein the bone part moving assembly and the bone attachment assembly have the same construction.

In one form, the bone part moving assembly and bone attachment assembly are mirror images of each other.

In one form, the frame and guide assembly are configured to define a capture rail arrangement.

In one form, the invention is directed to a system for changing a configuration of a bone having a length. The system includes: a bone plate having a length between first and second ends; a guide assembly on the bone plate; a bone part moving assembly; and a fixation element. The guide assembly and bone part moving assembly are configured so that a part of the bone part moving assembly is guided in a controlled path along the length of the bone plate. The bone part moving assembly further includes a fixation element support with a fixation element mount configured to support the fixation element and allow the supported fixation element to be directed into bone without passing through the bone plate. The fixation element is caused to move with the part of the bone part moving assembly together with a bone region into which the fixation element is directed. With a first part of the bone plate fixed to one bone portion, another bone portion movable relative to the one bone portion, and into which the fixation element is directed, can be moved by manipulating the bone part moving assembly, guidingly toward the one bone portion by following movement of the part of the bone part moving assembly in the controlled path.

In one form, the guide assembly is integrally formed with the bone plate.

In one form, the guide assembly is separate from, and attached to, the bone plate.

In one form, the guide assembly consists of one of an elongate rail and an elongate slot.

In one form, the guide assembly has an elongate rail. The part of the bone part moving assembly defines a slot for the elongate rail and captively engages the elongate rail.

In one form, the guide assembly has an elongate plate that extends over a majority of the length of the bone plate.

In one form, the elongate plate extends substantially fully between the first and second ends of the bone plate.

In one form, the part of the bone part moving assembly has a frame. The fixation element support and frame are configured so that the fixation element mount can be moved guidingly relative to the frame to change a position of the fixation element mount relative to the frame.

In one form, the system is provided in combination with a bone attachment assembly configured to be engaged with the guide assembly and fixed to a bone at a location spaced from a location at which the fixation element is directed into a bone.

In one form, the bone attachment assembly and guide assembly are configured so that the bone attachment assembly is guided in a predetermined path along the length of the bone plate.

In one form, the bone attachment assembly has a second fixation element support with a second fixation element mount.

In one form, the bone attachment assembly has a frame that is configured to cooperate with the guide assembly to guide the frame in the predetermined path. The second fixation element support is mounted on the frame.

In one form, the bone attachment assembly and frame are configured so that the second fixation element support can be moved guidingly relative to the frame.

In one form, the bone part moving assembly and bone attachment assembly have the same construction.

In one form, the bone part moving assembly and bone attachment assembly are mirror images of each other.

In one form, the elongate plate has an elongate opening therethrough extending over a majority of the length of the bone plate.

In one form, the bone plate has a surface. The elongate plate has a surface that conforms to and is placed against the bone plate surface. Oppositely projecting flanges define a guide rail along which the part of the bone part moving assembly is guided in the controlled path.

In one form, the bone plate has a plurality of through openings in registration with the elongate opening in the elongate plate whereby fasteners can be selectively directed through the elongate opening and the plurality of through openings in the bone plate and into a bone.

In one form, the fixation element is a fixation pin that can be translated relative to the fixation element mount and into bone.

BRIEF DESCRIPTION OF THE DRAWINGS

FIG. 4 is a perspective view of one form of bone plate, as shown schematically in FIG. 2;

FIG. 5 is an end elevation view of the bone plate in FIG. 4;

FIG. 6 is a side elevation view of the bone plate in FIGS. 4 and 5;

FIG. 7 is a plan view of an elongate plate making up the guide assembly on the system in FIG. 2;

FIG. 8 is a side elevation view of the plate in FIG. 7;

FIG. 9 is a perspective view of the plate in FIGS. 7 and 8;

FIG. 10 is a view as in FIG. 9 but from a different perspective;

FIG. 11 is an end elevation view of the plate in FIGS. 7-10;

FIG. 12 is a plan view showing the bone plate in FIGS. 4-6 and plate in FIGS. 7-11 operatively connected;

FIG. 16 is a perspective view of the components in FIGS. 12-15 together with one form of bone part moving assembly as shown schematically in FIG. 2;

FIG. 17 is a plan view of the bone part moving assembly in FIG. 16;

FIG. 18 is an end elevation view of the bone part moving assembly in FIGS. 16 and 17;

FIG. 19 is a side elevation view of the bone part moving assembly in FIGS. 16-18;

FIGS. 20-22 are different perspective views of the bone part moving assembly in FIGS. 16-19;

FIG. 23 is a side elevation view of the components as in FIG. 16 and additionally including a bone attachment assembly, according to the invention, operatively connected to the plates as shown in FIG. 12;

FIG. 24 is an end elevation view of the components in FIG. 23;

FIG. 32 is a view as in FIG. 29 wherein the bone sections have been moved against each other;

FIG. 33 is a view as in FIG. 32 with a bone plate fixed to the bone sections to complete the bone shortening procedure; and FIG. 34 is a schematic representation of a clamping arrangement for maintaining system parts fixed relative to a respective bone part.

DETAILED DESCRIPTION OF THE PREFERRED EMBODIMENT

The present invention relates to both a method and system for changing the configuration of a bone. While prior art is described above in relationship to an ulnar osteotomy, the invention relates generically to any bone that is commonly reconfigured as through the performance of an osteotomy. Further, while the invention will be described with respect to an osteotomy involving shortening of a bone, the invention is not so limited and the structure and steps described herein are equally applicable and adaptable to other procedures, including but not limited to, lengthening.

Figure 1:
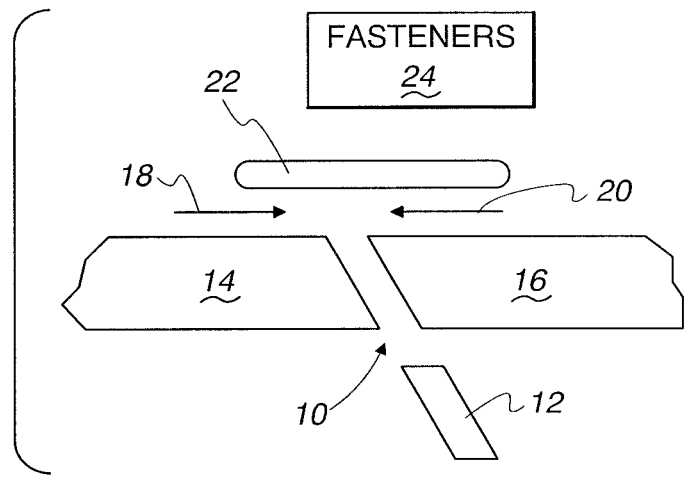
FIG. 1 is a schematic representation of a bone that has been cut to remove a fragment thereof and in relationship to a bone plate securable to separated bone portions by fasteners.

The invention will be described with respect to a bone 10, as shown schematically in FIG. 1, that is cut strategically to remove a bone fragment 12. This produces first and second bone sections/parts 14, 16 that are thereafter urged against each other, as indicated by the arrows 18, 20. In the desired end relationship, the bone sections 14, 16 are held together by a spanning bone plate 22 fixed to the bone sections 14, 16 by appropriate fasteners 24. Individual fasteners may be directed through the bone plate 22 into one of the bone sections 14, 16 and/or into both bone sections 14, 16.

The focus herein will not be on the details concerning cutting of the bone 10, but rather repositioning and fixation of the bone sections 14, 16 after cutting, regardless of how that cutting is performed. Bone section repositioning and fixation are accomplished using the inventive system, as shown schematically at 26 in FIG. 2.

The system 26 consists of the aforementioned bone plate 22, a guide assembly 28 on the bone plate 22, and a bone part moving assembly 30. The guide assembly 28 and bone part moving assembly 30 are configured so that a part 32 of the bone part moving assembly 30 is guided in a controlled path along the length of the bone plate 22.

The system additionally includes a fixation element 34.

The bone part moving assembly 30 further includes a fixation element support 36 with a fixation element mount 38 configured to support the fixation element 34 and allow the support and fixation element 34 to be directed into bone without passing through the bone plate 22. Through this arrangement, the fixation element 34 is caused to move with the part 32 of the bone part moving assembly 30 together with a bone region into which the fixation element 34 is directed.

With this construction, with a first part of the bone plate 22 fixed to one bone portion, another bone portion movable relative to the one bone portion, and into which the fixation element is directed, can be moved as by manipulating the bone part moving assembly, guidingly toward the one bone portion by following movement of the part 32 of the bone part moving assembly 30 in its controlled path.

Figure 2:
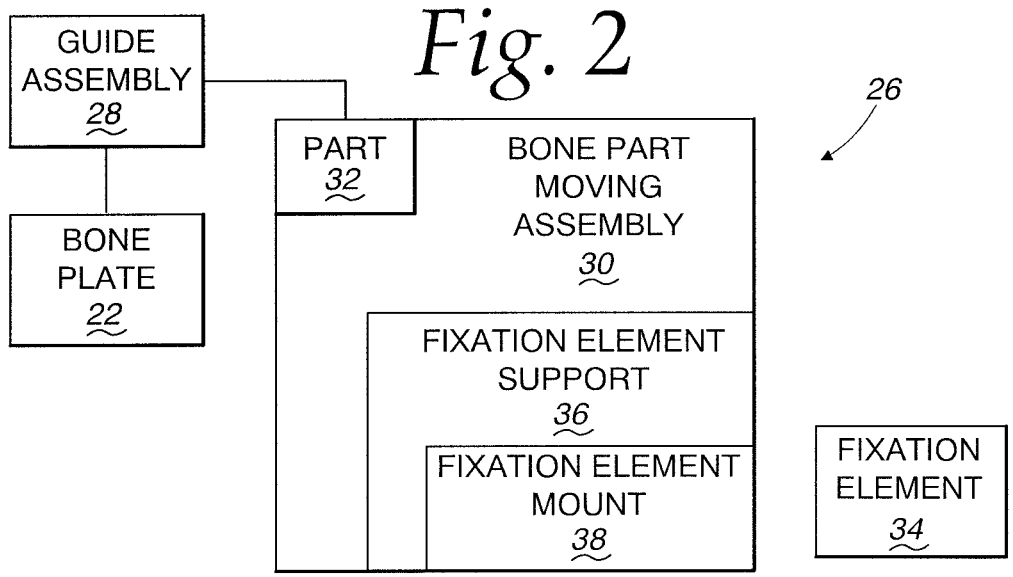
FIG. 2 is a schematic representation of a system for changing a configuration of a bone, according to the invention.
Figure 3:
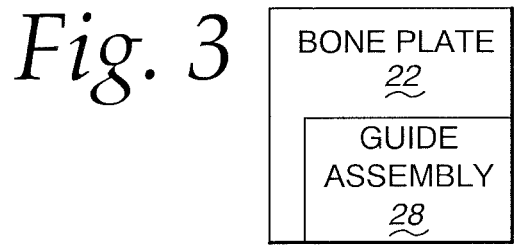
FIG. 3 is a schematic representation of an alternative form of bone plate and guide assembly on the system in FIG. 2.
Figure 13:
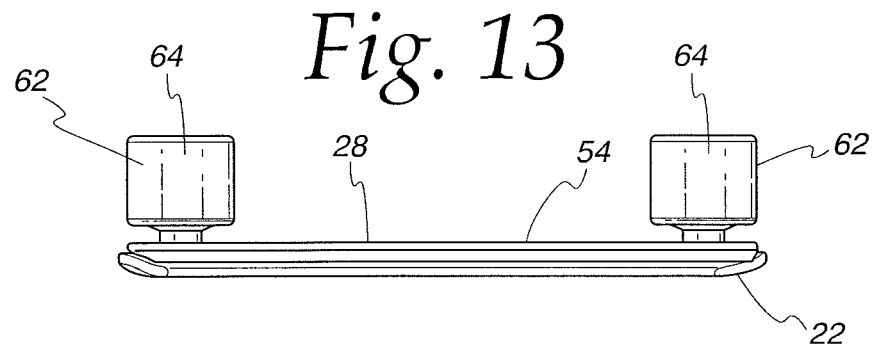
FIG. 13 is a side elevation view of the components in FIG. 12.

As shown in FIG. 3, the guide assembly 28 may be integrally formed with the bone plate 22 as opposed to being separate from, and attached to, the bone plate 22, as shown in FIG. 2.

The schematic representation of the system 26 is intended to encompass the specific forms thereof described hereinbelow, as well as virtually an unlimited number of variations of the components thereof and their interaction. Exemplary forms of the invention will now be described with respect to FIGS. 4-27 and 29-33, with it being understood that these specific forms are exemplary in nature only.

A specific form of the bone plate 22 is shown in FIGS. 4-6. The bone plate 22 has a body 40 with a length, as indicated by the double-headed arrow 42, between opposite ends 44, 46.

The body 40 has oppositely facing surfaces 48, 50, with the former either flat or curved to at least nominally match the contour of the region of the bone 10 which it overlies and to which it is fixed. The oppositely facing surface 50 has a complementary curvature so as to define a substantially uniform thickness T between the surfaces 48, 50 over the full width of the bone plate 22.

A plurality of through openings 52 are provided to accommodate the fasteners 24.

In this embodiment, the guide assembly 28 consists of at least an elongate plate, as shown at 54, in FIGS. 7-11. The elongate plate 54 is shown attached to the bone plate 22 in FIGS. 12-15.

Figure 14:
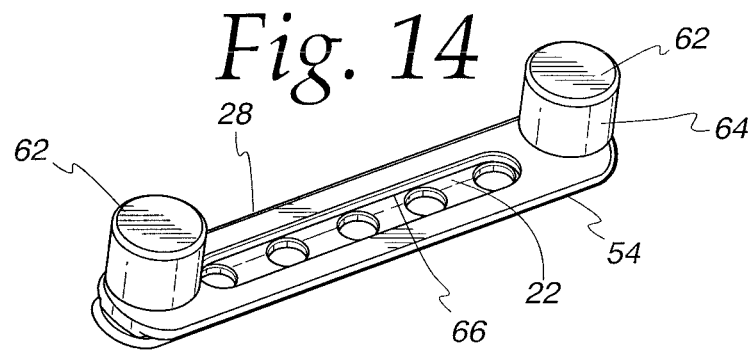
FIG. 14 is a perspective view of the components in FIGS. 12 and 13.

The perimeter shape of the elongate plate 54 is nominally matched to the perimeter shape of the bone plate 22, as viewed in plan, as seen most clearly in FIGS. 12 and 14. The elongate plate 54 extends preferably over at least a majority of the length of the bone plate 22. As depicted, the elongate plate 54 extends substantially fully between the spaced ends 44, 46 of the bone plate 22.

In this embodiment, the bone plate 22 has seven through openings 52, equidistantly spaced along the length of the bone plate 22, with endmost through openings 52a, 52b adjacent the ends 44, 46 of the bone plate body 40.

The elongate plate 54 has discrete openings 56a, 56b respectively adjacent its lengthwise ends 58, 60, with the openings 56a, 56b respectively registrable with the bone plate openings 52a, 52b. While the openings 56a, 56b are shown to be round, they could have a slotted configuration to facilitate assembly. Threaded fasteners 62 are directed through the aligned openings 52a, 56a; 52b; 56b to secure the elongate plate 54 fixedly to the bone plate 22. The fasteners 62 have enlarged heads 64 that can be conveniently grasped and allow a substantial torque to be applied without tools to tighten and release the fasteners 62.

The elongate plate 54 has an elongate opening 66 therethrough extending over a majority of the length of the bone plate 54. With this arrangement, a plurality, and in this case five, of the through openings 52 on the bone plate 22 register with the elongate opening 66, whereby appropriate fasteners can be strategically directed through the elongate opening 66 and the bone plate openings 52 and into bone.

The elongate plate 54 has a surface 68 that is curved to conform to the surface 50 of the bone plate 22 that it overlies. With this complementary surface arrangement, the connection of the elongate plate 54 to the bone plate 22 is stabilized. This matching shape is not required.

The elongate plate 54 has oppositely projecting flanges 70, 72 that cooperatively define a guide rail that makes up the guide assembly 28 for the part 32 of the bone part moving assembly 30.

Further details of the exemplary guide assembly 28 and bone part moving assembly 30 are shown in FIGS. 16-27.

The bone part moving assembly 30 consists of a frame 74. The frame 74 has a cylindrical body 78 from which the part 32 projects in cantilever fashion. The part 32 has a generally squared shape with a flat wall 80 with four depending legs 82a, 82b, 82c, 82d that are return bent to project so as to cooperatively define a T-shaped slot 84, in conjunction with the flat wall 80, as seen from the FIG. 18 perspective. In this embodiment, four legs are shown. However, two legs projecting towards each other would suffice.

The slot 84 is configured to slidably receive the rail defined cooperatively by the flanges 70, 72. This is a captive rail arrangement in which relative movement between the rail and frame part 32 is confined to translational movement parallel to the lengths of the bone plate 22 and elongate plate 54. Accordingly, as seen in FIG. 16, the part 32 is guided by the rail in the aforementioned controlled path, as indicated by the double-headed arrow P. Accordingly, precise controlled relative movement of bone portions can be effected in a linear path.

Figure 15:
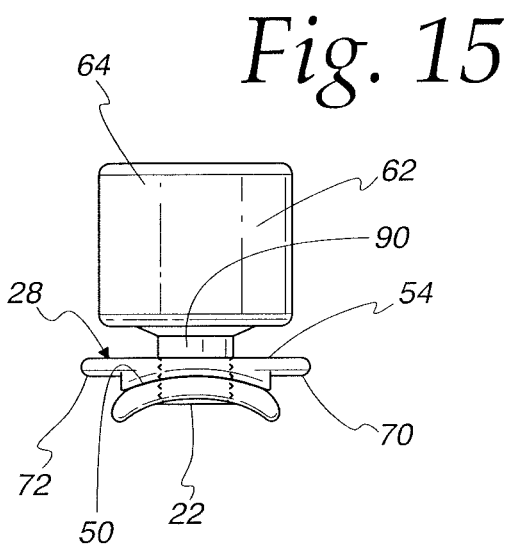
FIG. 15 is an end elevation view of the components in FIGS. 12-14.
Figure 25:
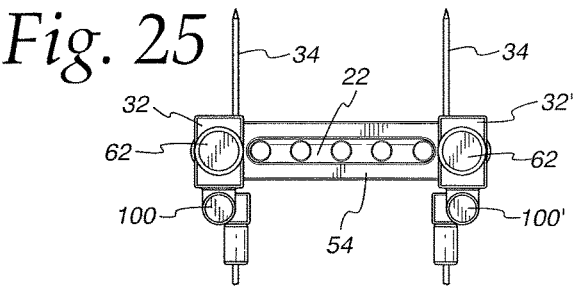
FIG. 25 is a plan view of the components in FIGS. 23 and 24.
Figure 26:
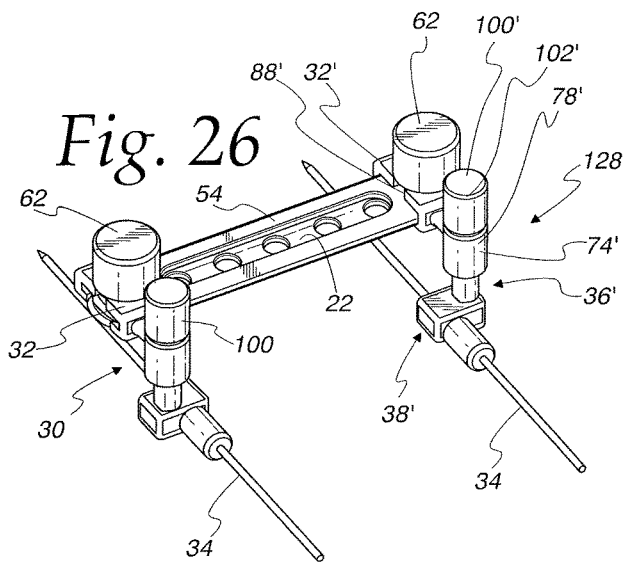
FIG. 26 is a perspective view of the components in FIGS. 23-25.

In this embodiment, the frame part 32 has a U-shaped slot/opening 88 through which one of the fasteners 62 extends. Once tightened, the spaced fasteners 62 sandwich the plate 54 to the bone plate 22 and capture the guide frame part 32. With the fasteners 62 loosened slightly, the frame part 32 can be moved in a guided fashion lengthwise of the plate 22, while the fasteners 62 still hold the elongate plate 54 to the bone plate 22. As seen in FIG. 15, a neck 90 of the fastener 62 is movable into and out of the slot/opening 88 whereby the frame part 32 can be advanced lengthwise to adjacent one end of the combined bone plate 22 and elongate plate 54, as shown in FIG. 16. With the fastener 62 extended through the frame part 32 as shown, the neck 90 thereon is guided within the slot/opening 88. At one extreme in the range of movement of the part 32—towards the left side in FIG. 16—the neck abuts the base 92 of the slot/opening 88.

The bone part moving assembly 30 is movable away from the FIG. 16 position to a position wherein the frame part 32 abuts the fastener 62 at the opposite end of the combined bone plate 22 and elongate plate 54.

The fixation element support 36 consists of an elongate body 94 that slides guidingly within the cylindrical body 78 in a line indicated by the double-headed arrow 96 in FIG. 18. The body 94 has a flat thereon that engages a complementary flat 95 on the cylindrical body 78 to make a keyed connection and thereby prevent relative turning of the cylindrical body 78 and the body 94 about their common axis 98. Any other keying arrangement is contemplated.

An adjusting component 100 rests, and is maintained, against the top of the cylindrical body 78 and is threadably engaged with the body 94. The component 100 is turned in opposite directions to move the body 94 in opposite directions along the path indicated by the double-headed arrow 96 relative to the frame 74. It is not necessary to show the details of this structure, as this type of adjusting mechanism is well known and may take many different forms. An enlarged head 102 is provided to input the turning torque and is made to be readily graspable between the fingers of a user. Accordingly, by turning the head 102 in opposite directions, the body 94 can be selectively raised and lowered relative to the frame part 32, as shown in FIG. 18.

The lower region of the body 94 defines the fixation element mount 38 which accommodates a stepped diameter sleeve 104 for supporting the fixation element 34, which in this embodiment is in the form of a fixation pin. With the fixation element 34 supported on the fixation element mount 38, the sharpened leading edge 106 of the fixation element 34 can be advanced progressively into the bone in the direction of the arrow 108. The fixation element 34 is thus directed into the bone without passing through the bone plate 22. Once the fixation element 34 is directed into the bone, that region of the bone moves together with the fixation element 34, the fixation element support 36, and the frame 74, including the part 32 that is guided in the controlled path along the length of the bone plate 22.

It should be mentioned that the use of only one fixation element/pin 34 is but one possible system configuration. For more rigid fixation, two or more fixation elements 34 may be accommodated that are directed into the bone in either parallel directions, or in non-parallel orientations for improved fixation.

The invention also contemplates different variations of holding structure. As one example, a bone clamp on either side could clamp the part 32 to bone.

Figure 27:
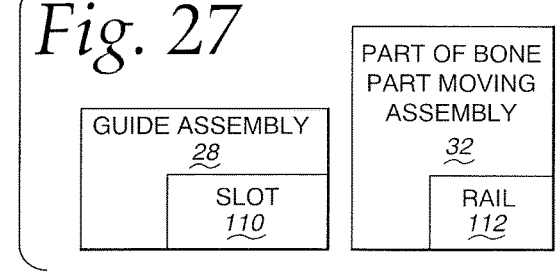
FIG. 27 is a schematic representation of alternative cooperating structure between the guide assembly and part of the bone part moving assembly, as shown schematically in FIG. 2.

Further, it should be noted that the formation of the guide rail on the guide assembly is but one of different alternative constructions contemplated. For example, as shown in FIG. 27, the guide assembly 28 might define a slot 110 in which a rail 112 on the part of the bone part moving assembly 32 moves. In other words, a reversal of elements would cause the cooperating structures to be guided in the same manner.

Still further, the generic showing of the guide structure is not limited to a basic rail and slot arrangement. One typical design would be a tongue-in-groove type connection of the part 32 to the track. In another variation, one or more pins, rails, or tracks extend from a connecting element on one side of the plate to capture the part 32 on the opposite side.

Figure 28:
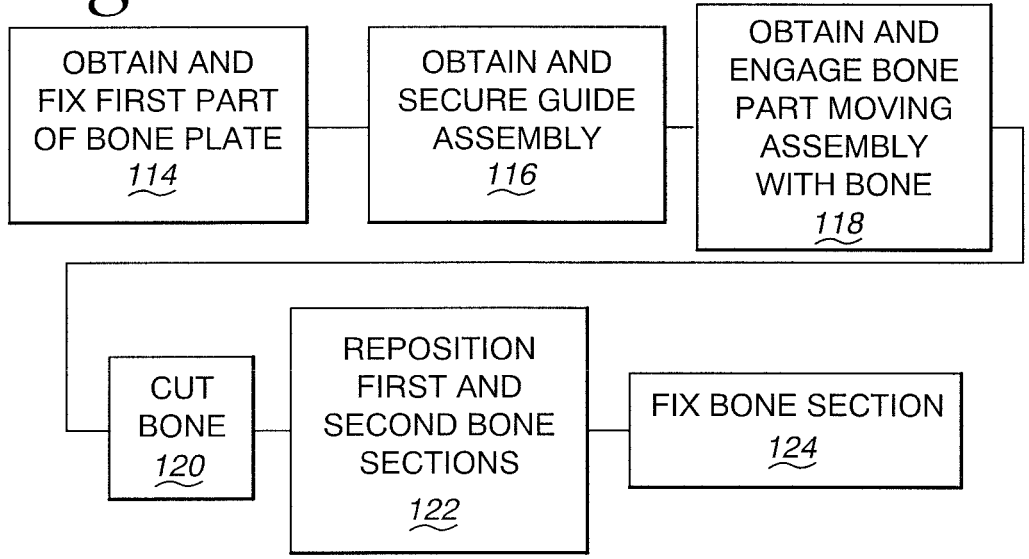
FIG. 28 is a flow diagram representation of a method of changing a configuration of a bone, according to the present invention.

With the above system, a method of changing a configuration of a bone having a length can be practiced, as shown in flow diagram form in FIG. 28. As shown at block 114, a bone plate having a length is obtained and a first part thereof is fixed to the bone at a first bone location.

As shown at block 116, a guide assembly is obtained and secured in an operative position in relationship to the bone.

As shown at block 118, a bone part moving assembly is obtained and is configured so that at least part of the bone part moving assembly cooperates with the guide assembly to be guided by the guide assembly in a controlled path. The bone part moving assembly is engaged with the bone at a second bone location spaced from the first bone location.

As shown at block 120, the bone is cut to define first and second bone sections and so that the bone part moving assembly engages the second bone section and the first bone location is on the first bone section.

As shown at block 122, the first and second bone sections are relatively repositioned into a desired relationship, thereby causing the part of the bone part moving assembly to move guidingly, together with the second bone section, in the controlled path.

As shown at block 124, the first and second bone sections are fixed in the desired relationship.

The guide assembly and bone part moving assembly are configured so that with the guide assembly in the operative position and the bone part moving assembly engaged with the bone at the second location, the first and second bone sections can be controllably relatively moved without requiring guided movement of any component, that is extended through the bone plate and into the bone, lengthwise of the bone plate.

More specifically, with reference to the embodiment herein described, and with initial reference to FIG. 16, the method is carried out by fixing a first part of the bone plate 22 at a first bone location through fixation structure at 126. The fixation structure 126 might be a fastener, clamp, etc., and is not limited in form.

The fixation element 34 on the bone part moving assembly 30 is engaged with the bone at a second bone location spaced from the first bone location.

After effecting cutting of the bone, the defined first and second bone sections are moved into a desired relationship, by lengthening, shortening, etc. As this occurs, the bone part moving assembly 30, together with the bone region engaged by the fixation element 34, follow guided movement of the bone part moving assembly part 32 in its controlled path, as indicated by the double-headed arrow P. The bone part moving assembly 30 may be directly manipulated as this repositioning is effected, or the bone portion penetrated by the fixation element 34 may be otherwise manipulated into the desired end position.

As noted above, the connection of the bone part moving assembly 32 to its respective bone region is effected without requiring that the fixation element 34, or any other component, be extended through the bone plate 22 and into bone.

Commonly, the fixation structure 126 will be in the form of the fasteners 24, that may be threaded to be advanced through the bone plate openings and strategically into the bone.

Once the fixation of the formed bone sections in the desired relationship is established and fixed, all of the components in FIG. 16 may be removed, leaving only the bone plate 22 in place, held by appropriate fixation structure.

The ability to reposition the fixation element support 36 and fixation element mount 38 thereon relative to the frame 74 allows the surgeon to select an optimal entry location for the fixation element 34 to effect the most stable connection of the bone part moving assembly 30. A range of potential entry locations is made possible by this construction.

In one form, the fixation structure 126 is made up of a bone attachment assembly 128, as shown in FIGS. 23-26. The bone attachment assembly 128 has essentially the same components and component function as the bone part moving assembly 30. The only significant difference in the depicted embodiment is that the bone attachment assembly 128 is a mirror image of the bone part moving assembly 30.

The parts of the bone attachment assembly 128 will now be identified with reference numerals corresponding to those identifying parts on the bone part moving assembly 30, but with a "'" designation added.

The bone attachment assembly 128 has a frame 74' with a cylindrical body 78' from which a part 32' projects. The frame 74' is slidably connected to a fixation element support 36' which has a fixation element mount 38' for a fixation element 34. An adjustable turning arrangement is provided with an adjusting component 100' to reposition the fixation element support 36' relative to the frame 74' and is operable through an enlarged head 102'. The part 32' has an elongate slot/opening 88' to accommodate the neck 90 (FIG. 15) of the fastener 62 that extends therethrough.

While the bone attachment assembly 128 might be movable into different positions relative to the combined bone plate 22 and elongate plate 54, and fixed in those positions, in the embodiment shown, the bone attachment assembly 128 is fixed in a single position.

Each of the parts 32, 32' has an undercut 130, as shown for the part 32 in FIG. 17, which accepts a complementarily-shaped part of the respective fastener 62. By tightening respective fasteners 62, the parts 32, 32' can be fixed rigidly against movement lengthwise relative to the combined bone plate 22 and elongate plate 54.

With this configuration, either of the parts 32, 32' can be fixed relative to the combined bone plate 22 and elongate plate 54 while the other part 32, 32' can be movable along the length of the combined bone plate 22 and elongate plate 54. Thus, the surgeon has the option of sliding bone portions from either the left or the right depending upon which direction he/she would like the osteotomy cut.

The surgeon further has the option of using only one of the assemblies 30, 128 at either side of the bone plate 22 to perform a procedure. The side of the bone plate 22 from which the assembly 30, 128 is absent can be suitably fixed to the bone 10 using conventional fasteners, such as bone screws. This makes the overall system more compact, which may facilitate assembly and use.

Thus, by changing which of the parts 32, 32' is fixed, the bone part moving assembly 30 performs the function of the bone attachment assembly 128 and vice versa. For purposes of simplicity, a distinction is made throughout the drawings and in the Detailed Description between the bone part moving assembly 30 and bone attachment assembly 128 when in fact, as depicted, they are each, structurally and functionally, both a bone part moving assembly and bone attachment assembly, determined by which of the parts 32, 32' is fixed and which of the parts 32, 32' is allowed to guidingly move in use. Of course, these assemblies need not have the same construction or the particular configurations depicted.

The bone attachment assembly 128 is engaged with its respective bone region by selecting the desired entry location for the fixation element 34 and translating the same into the bone.

The bone part moving assembly 30 and bone attachment assembly 128 can be directly manipulated to effect movement of the respective bone portions. Alternatively, one or both of the bone portions can be otherwise manipulated (i.e., not directly through the bone part moving assembly 30 or bone attachment assembly 28).

A method of shortening a bone will now be described with respect to FIGS. 29-33 with an assembly 128" fixable to the bone section 16 and performing the function of the bone part moving assembly 30 in the earlier described embodiment.

The method utilizes the bone plate 22 and associated guide assembly plate 54.

In this embodiment, a modified form of fastener 62" is utilized to perform the function of the aforementioned fastener 62. The fastener 62" has an enlarged head 64" with a radially enlarged bead 150 that can be grasped to facilitate hand tightening and loosening. A head extension 152 has a receptacle 154 to accept a fitting 156 on a tool 158 that can be used to turn the head 64".

Figure 29:
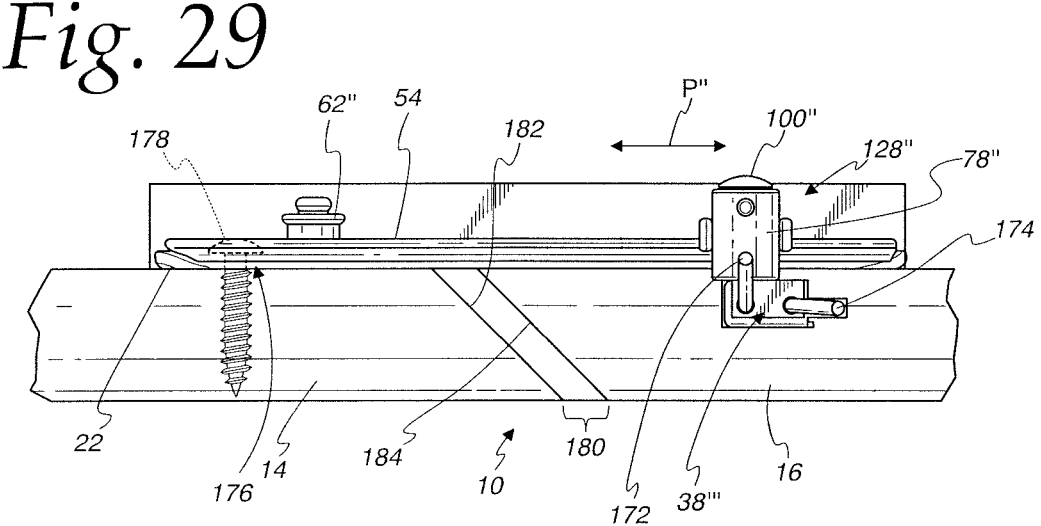
FIG. 29 is a side elevation view showing one form of the inventive system set up to guidingly draw two bone sections towards each other to close a gap created by the removal of a bone fragment.
Figure 31:
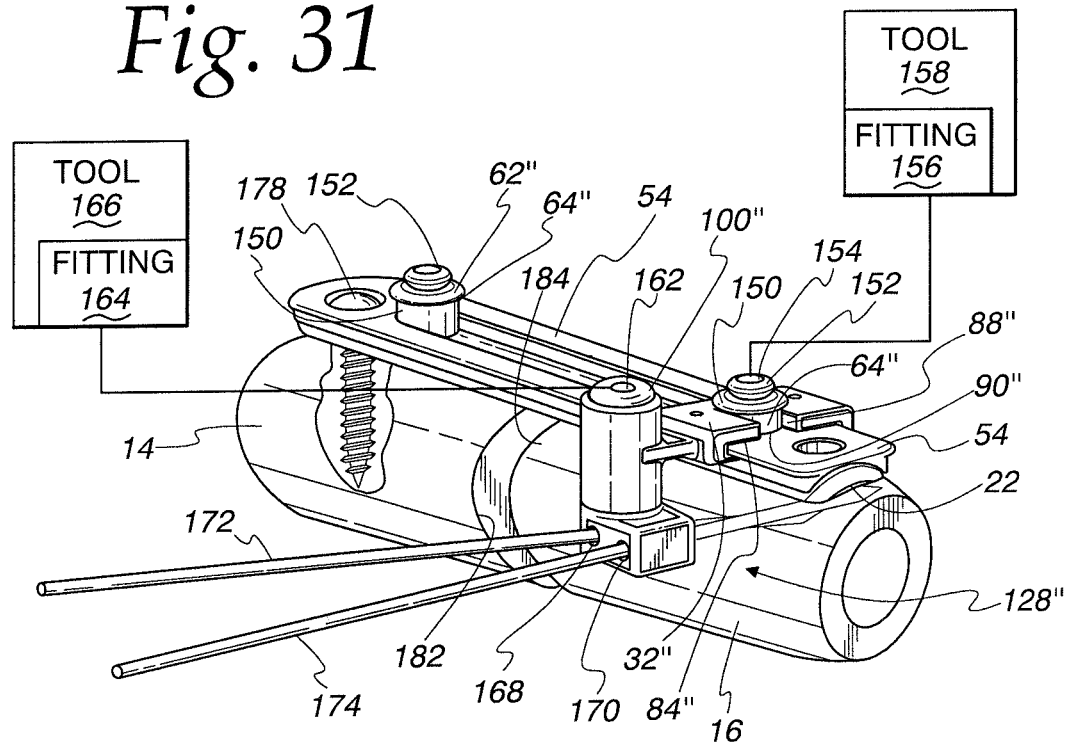
FIG. 31 is a perspective view of the components in FIGS. 29 and 30.

The assembly 128" is engaged with the head 64" on the fastener 62" located above the bone section 16, as seen in FIGS. 29 and 31. The assembly 128" has a frame 74" with a cylindrical body 78" from which a part 32", corresponding to the part 32, projects in cantilever fashion.

The part 32" defines a T-shaped slot 84" to slidably receive the rail defined on the plate 54. The rail and slot 84" cooperate to guide translational movement of the part 32" parallel to the aligned lengths of the bone plate 22 and elongate plate 54 in a controlled path, as indicated by the double-headed arrow P". As the assembly 128" is moved from left to right in FIGS. 31 and 32, a head part/neck 90" on the fastener 62" moves into a U-shaped slot/opening 88" defined by the part 32", This defines one limit on the range of movement of the part 32"; the position for the part 32" at which the procedure is initiated, as shown in FIGS. 31 and 32.

A fixation element support 36" consists of an elongate body 94" that slides guidingly within the cylindrical body 78" in a line indicated by the double-headed arrow 160. The body 94" is keyed against turning around its length within the cylindrical body 78" by providing one or more flats/keying elements (not shown), such as the flat 95 on the body 94 in the previously described embodiment.

An adjusting component 100" is turned to move the body 94 in opposite directions along the path indicated by the double-headed arrow 160 relative to the frame 74". The same arrangement of components can be incorporated as in the prior embodiment that is controlled by the adjusting component 100.

In this embodiment, rather than having a graspable adjusting component 100, the adjusting component 100" has a lower profile head and a receptacle 162 therein to accept a fitting 164 on a tool 166 that can be used to turn the component 100" in opposite directions to thereby selectively raise and lower a fixation element mount 38" at the bottom of the body 94".

Figure 30:
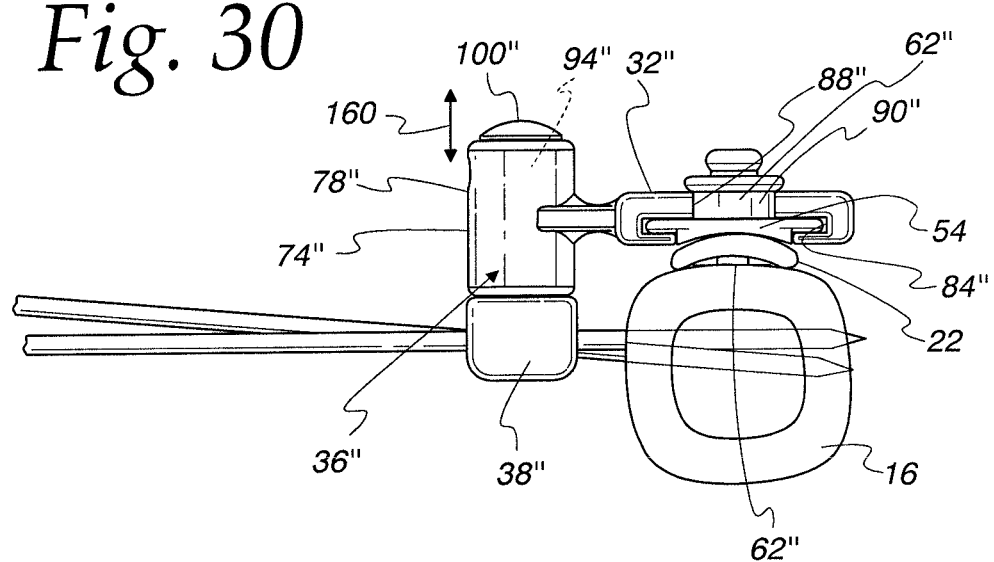
FIG. 30 is an end elevation view of the components in FIG. 29.

In this embodiment, the fixation element mount 38" has separate passages 168, 170 to each accept a fixation element 172, 174, respectively, that can be directed at different angles, as seen in FIGS. 30 and 31, into the bone section 16 to thereby fix the assembly 128" with respect to the bone section 16.

As indicated above, the invention is not concerned with the precise manner of removing the bone fragment 12 or the coordination of placement of the inventive components thereon to reposition the bone sections 14, 16. It suffices to say that with the bone fragment 12 removed, as shown in FIG. 29, a first part 176 of the bone plate 22 is fixed to the bone section 14 at a first location. While the fixation is accomplished in the embodiment shown by directing a threaded fixation element 178 through the plate 22 and into the bone section 14, as noted above, any other manner of fixing the plate 22 to the bone section 14 is also contemplated.

By directly or indirectly manipulating the assembly 128", the bone sections 14, 16 can be relatively moved to close the gap region at 180 produced by the removal of the bone fragment 12 while precisely maintaining the relationship otherwise existing between the bone sections 14, 16 before the bone fragment 12 is removed. This relative movement can be effected by moving either bone section 14, 16 towards the other or moving both bone sections 14, 16 towards each other. In any event, the relative movement causes the bone section 16 to move in a controlled path caused by the controlled guided movement of the part 32" of the assembly 128" along the guide rail defined by the plate 54.

The above-described structure can also be utilized to perform the process, substantially as described above, while permitting a controlled degree of relative turning of the bone parts 14, 16 about their lengths, preparatory to fixation. This can be accomplished as by re-fixing the bone part 16 relative to the part 32", as through the fixation elements 172, 174, once cutting through the bone 10 is effected. Alternatively, the fixation element mount 38" might be made movable relative to the part 32" to allow this reorientation of the bone part 16 relative to the bone part 14.

As also noted above, the fixation element mount 38" can be translated along the line of the arrow 160 to define the optimal location at which the fixation element mount 38" can be rigidly fixed to the bone section 16 using the fixing elements 172, 174. Accordingly, the bone section 16 can be stably guided by the assembly 128" along the rail on the plate 54 to bring parallel bone surfaces 182, 184, respectively on the bone sections 14, 16, into aligned, facial, abutting relationship as shown in FIG. 33. This can be accomplished without requiring any other connection of the plate 22 to the bone section 16 as might compromise the bone section 16 and weaken a subsequent connection with the bone plate 22. As mentioned earlier, the need to direct any guiding component through the plate 22 and into the bone 10 may be avoided.

Once the bone configuration of FIG. 33 is realized, appropriate fastening elements 178 can be directed through the plate 22 and into the bone sections 14, 16 to complete the procedure.

The assembly 128" can be removed after the appropriate rigidity between the bone sections 14, 16 is maintained.

In this embodiment, one of the plate openings 186, and a cooperating fixation element 188, are configured to allow the fixation element 188 to be an interfragmentary fastener that extends through each bone section 14, 16 across the oblique cut line 190.

As noted above, the invention contemplates myriad variations of the basic structure, described in exemplary forms above. As just one additional example, as shown in FIG. 34, one or more of the parts 32, 32', 32" may be fixed to move as one piece with its respective bone part using a clamping arrangement, shown at 200. As depicted schematically therein, a part $32^{3'}$, generically representing the parts 32, 32', 32", and others, is held fixedly against its respective bone part 14, 16 by cooperating clamp parts 202 which cooperate to captively engage the bone parts 14, 16.

The system provides a precise, controlled shortening without requiring a slotted bone screw hole in the plate. This results in a plate design that can be as short as needed and allows the amount of shortening to be as long as desired. The system allows the cut orientation to be made in whichever direction that the surgeon desires, and can be used with or without the placement of a lag screw. In addition, bone screws may be directed through the plate and into bone only a single time, and are not repetitively inserted, loosened, and re-tightened, resulting in more reliable thread purchase. Moreover, the system allows a design with or without utilization of an oblique lag screw across the osteotomy. The system also allows a design that can be used at the end of the bone. As a result, the plate length can be as short as desired, allows a uniform distribution of screw fixation, and allows a lag screw as an independent design option, while simplifying the procedure to only a limited number of steps. Moreover, since no slots need be present, the screw fixation can be placed close to both sides of the osteotomy site, improving fixation. In addition, the direction of the osteotomy cut can be offered in either direction at the preference of the surgeon, and it eliminates the need for asymmetric, lopsided plate configurations that exist with many current designs.

The foregoing disclosure of specific embodiments is intended to be illustrative of the broad concepts comprehended by the invention.

The invention claimed is:

1. A method of changing a configuration of a bone having a length, the method comprising the steps of:
obtaining a bone plate having a length;
fixing a first part of the bone plate to the bone at a first bone location;
obtaining a guide assembly;
securing the guide assembly in an operative position in fixed relationship to the bone;
obtaining a bone part moving assembly configured so that at least a part of the bone part moving assembly cooperates with the guide assembly to be guided in a controlled path by the guide assembly;
engaging the bone part moving assembly with the bone at a second bone location spaced from the first bone location;
cutting the bone to define first and second bone sections and so that the bone part moving assembly engages the second bone section and the first bone location is on the first bone section,
the bone part moving assembly and guide assembly further configured to cooperate with each other so as to control relative turning of the first and second bone sections around the length of the bone to thereby maintain alignment of the first and second bone sections;
relatively repositioning the first and second bone sections into a desired relationship and thereby causing the part of the bone part moving assembly to move, together with the second bone section, guidingly in the controlled path; and
fixing the first and second bone sections in the desired relationship,
wherein the guide assembly and bone part moving assembly are configured to cooperate with each other so that with the guide assembly in the operative position and the bone part moving assembly engaged with the bone at the second location, relative movement of the first and second bone sections is guided in a direction lengthwise of the plate without requiring guided movement of any component extended through the bone plate.

2. The method of changing a configuration of a bone according to claim 1 wherein the guide assembly is integrally formed with the bone plate.

3. The method of changing a configuration of a bone according to claim 1 wherein the guide assembly is separate from, and attached to, the bone plate.

4. The method of changing a configuration of a bone according to claim 1 wherein the bone plate has at least one through opening to receive a fastener and the step of fixing the first and second bone sections in the desired relationship comprises obtaining at least one fastener and directing the at least one fastener into the at least one through opening in the bone plate and into the bone.

5. The method of changing a configuration of a bone according to claim 1 further comprising the step of separating and removing at least part of the bone part moving assembly after fixing the first and second bone sections in the desired relationship.

6. The method of changing a configuration of a bone according to claim 1 wherein the step of securing the guide assembly in an operative position comprises securing the guide assembly to the bone plate.

7. The method of changing a configuration of a bone according to claim 6 wherein the rail and cooperating slot are configured to produce a captive rail arrangement.

8. The method of changing a configuration of a bone according to claim 1 wherein there is an elongate rail on one of the guide assembly and the part of the bone part moving assembly and a cooperating slot on the other of the guide assembly and the part of the bone part moving assembly, and the step of relatively positioning the first and second bone sections causes guided movement of the rail within the cooperating slot to thereby cause the part of the bone part moving assembly to be guided in the controlled path.

9. The method of changing a configuration of a bone according to claim 8 wherein the part of the bone part moving assembly comprises a frame, the step of fixing the guide plate to the bone plate comprises directing a fastener through the guide plate and into the bone plate and the frame has an opening through which the fastener extends.

10. The method of changing a configuration of a bone according to claim 8 wherein the bone part moving assembly comprises a fixation element support and the step of engaging the bone part moving assembly with the bone at the second location comprises directing a fixation element, supported by the fixation element support, into the bone at the second location whereby the fixation element follows movement of the part of the bone part moving assembly in the controlled path.

11. The method of changing a configuration of a bone according to claim 10 wherein the part of the bone part moving assembly is part of a frame, the fixation element support has a fixation element mount and the frame and fixation element support are configured so that the fixation element support is movable guidingly relative to the frame and further comprising the step of moving the fixation element support relative to the frame so that the fixation element mount is at a desired location, within a range of potential locations after which the fixation element is directed into the bone.

12. The method of changing a configuration of a bone according to claim 11 further comprising the step of manipulating the bone part moving assembly to thereby effect relative repositioning of the first and second bone sections.

13. The method of changing a configuration of a bone according to claim 1 further comprising the steps of obtaining a bone attachment assembly, engaging the bone attachment assembly with the guide assembly, and manipulating the bone part moving assembly and the bone attachment assembly to thereby effect relative repositioning of the first and second bone sections.

14. The method of changing a configuration of a bone according to claim 13 wherein the bone attachment assembly comprises a frame and the guide assembly and frame are configured so that the frame is movable guidingly relative to the bone plate along the length of the bone plate.

15. The method of changing a configuration of a bone according to claim 14 wherein the bone attachment assembly comprises a frame and a fixation element support with a fixation element mount, the frame and fixation element support configured so that fixation element support is movable guidingly relative to the frame and further comprising the step of moving the fixation element support relative to the frame so that the fixation element mount is at a desired location within a range of potential locations, after which the fixation element is directed into the bone.

16. The method of changing a configuration of a bone according to claim 14 wherein the frame and guide assembly are configured to define a capture rail arrangement.

17. The method of changing a configuration of a bone according to claim 14 further comprising the step of fixing the frame to the bone at a location spaced from the second bone location before manipulating the bone part moving assembly and the bone attachment assembly to effect relative repositioning of the first and second bone sections.

18. The method of changing a configuration of a bone according to claim 13 wherein the bone attachment assembly comprises a fixation element support and further comprising the step of directing a fixation element, supported by the fixation element support, into the bone without passing through the bone plate.

19. The method of changing a configuration of a bone according to claim 18 wherein the fixation element support has a fixation element mount and the frame and fixation element support are configured so that the fixation element support is movable guidingly relative to the frame and further comprising the step of moving the fixation element support relative to the frame so that the fixation element mount is at a desired location within a range of potential locations after which the fixation element is directed into the bone.

20. The method of changing a configuration of a bone according to claim 11 further comprising the step of obtaining a bone attachment assembly, engaging the bone attachment assembly with the guide assembly, and manipulating the bone part moving assembly and the bone attachment assembly to thereby effect repositioning of the first and second bone sections, wherein the bone part moving assembly and the bone attachment assembly have the same construction.

21. The method of changing a configuration of a bone according to claim 20 wherein the bone part moving assembly and bone attachment assembly are mirror images of each other.

* * * * *